US009637733B2

(12) United States Patent
Park et al.

(10) Patent No.: US 9,637,733 B2
(45) Date of Patent: May 2, 2017

(54) REAGENT SUPPLY DEVICE FOR ANALYSIS OF NUCLEIC ACID

(71) Applicant: Samsung Electronics Co., Ltd., Suwon-si, Gyeonggi-do (KR)

(72) Inventors: Chin-sung Park, Yongin-si (KR); Kak Namkoong, Seoul (KR); Joon-sub Shim, Yongin-si (KR); Won-seok Chung, Suwon-si (KR); Kyung-ho Kim, Seoul (KR); Joon-ho Kim, Seongnam-si (KR); Won-jong Jung, Seongnam-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 563 days.

(21) Appl. No.: 13/917,462

(22) Filed: Jun. 13, 2013

(65) Prior Publication Data

US 2014/0178982 A1 Jun. 26, 2014

(30) Foreign Application Priority Data

Dec. 21, 2012 (KR) .......................... 10-2012-0151340

(51) Int. Cl.
*C12N 15/10* (2006.01)
*B01L 3/00* (2006.01)

(52) U.S. Cl.
CPC .......... *C12N 15/1017* (2013.01); *B01L 3/527* (2013.01); *B01L 2300/0851* (2013.01); *B01L 2300/0861* (2013.01)

(58) Field of Classification Search
CPC ....... B01L 2300/087; B01L 2300/0861; C12N 15/1017

USPC ............................................ 435/306.1, 287.2
See application file for complete search history.

(56) References Cited

U.S. PATENT DOCUMENTS

| 4,769,333 | A | 9/1988 | Dole et al. | |
| 6,012,586 | A | * | 1/2000 | Misra ................... A61B 19/026 |
| | | | | 206/370 |
| 6,284,531 | B1 | * | 9/2001 | Zhu et al. .................. 435/305.3 |
| 6,410,275 | B1 | * | 6/2002 | Kluttz ..................... B01L 3/502 |
| | | | | 422/550 |
| 7,214,529 | B2 | 5/2007 | Kluttz et al. | |
| 7,225,949 | B2 | * | 6/2007 | Kubo et al. .............. 222/189.08 |

(Continued)

FOREIGN PATENT DOCUMENTS

| JP | 2001-235478 A | 8/2001 |
| JP | 2008-263959 A | 11/2008 |

(Continued)

OTHER PUBLICATIONS

European Patent Office, Extended European Search Report in European Patent Application No. 13184248.6, Mar. 13, 2014, 4 pp.

*Primary Examiner* — Michael Hobbs
*Assistant Examiner* — Liban Hassan
(74) *Attorney, Agent, or Firm* — Leydig, Voit & Mayer, Ltd.

(57) ABSTRACT

A reagent supply device includes a plurality of chambers which are separated from each other such that different reagents may be injected, the plurality of chambers having bottom surfaces made of a membrane, the membrane comprising a destruction pattern which is formed at a position corresponding to each of the plurality of chambers and breachable by an external impact to discharge the injected reagent from the chamber.

12 Claims, 8 Drawing Sheets

(56) References Cited

U.S. PATENT DOCUMENTS

| | | | |
|---|---|---|---|
| 2005/0226786 A1* | 10/2005 | Hager | B01J 19/0046 422/400 |
| 2005/0272169 A1* | 12/2005 | Griffin et al. | 436/514 |
| 2007/0026439 A1* | 2/2007 | Faulstich | B01F 13/0059 435/6.14 |
| 2008/0153714 A1 | 6/2008 | Hongo et al. | |
| 2008/0226508 A1* | 9/2008 | Byrnard et al. | 422/102 |
| 2010/0018915 A1* | 1/2010 | DiPrizio et al. | 210/455 |
| 2010/0120129 A1* | 5/2010 | Amshey | B01L 3/502715 435/270 |
| 2010/0233035 A1* | 9/2010 | Denawa et al. | 422/102 |
| 2011/0014687 A1* | 1/2011 | Nakamura et al. | 435/287.3 |
| 2011/0201099 A1* | 8/2011 | Anderson | G01N 21/05 435/287.2 |
| 2012/0115212 A1 | 5/2012 | Weigl et al. | |
| 2014/0050636 A1 | 2/2014 | Inoue et al. | |

FOREIGN PATENT DOCUMENTS

| | | |
|---|---|---|
| JP | 2009-002913 A | 1/2009 |
| KR | 1020040032422 A | 4/2004 |
| KR | 1020040043897 A | 5/2004 |
| KR | 1020080022025 A | 3/2008 |
| KR | 1020090079487 A | 7/2009 |
| KR | 1020120063162 A | 6/2012 |
| WO | WO 03-049860 A1 | 6/2003 |
| WO | WO 2012/147636 A1 | 11/2012 |

\* cited by examiner

REAGENT SUPPLY DEVICE FOR ANALYSIS OF NUCLEIC ACID

CROSS-REFERENCE TO RELATED APPLICATIONS

This application claims the benefit of Korean Patent Application No. 10-2012-0151340, filed on Dec. 21, 2012 in the Korean Intellectual Property Office, the entire disclosure of which is incorporated herein in by reference.

BACKGROUND

1. Field

The present disclosure relates to reagent supply devices for analysis of a nucleic acid.

2. Description of the Related Art

As point-of-care testing ("POCT") has become more widespread, the importance of gene analysis, external diagnosis, and gene sequence analysis is being emphasized and the demands therefore are gradually increasing. Recently, the availability of a molecular diagnosis method based on a nucleic acid in diagnosis of infectious diseases or cancers, pharmacogenomics, etc. has remarkably increased.

Meanwhile, to determine whether a specific DNA exists and to exactly determine the amount of DNA, a process of purifying/extracting a real sample and sufficiently amplifying the purified/extracted real sample to a measurable degree is performed. Among various gene amplification methods, for example, a polymerase chain reaction ("PCR") is most widely used. A process of preparing a nucleic sample for PCR includes an operation of capturing cells from a biological sample and an operation of extracting nucleic acids through lysis of cells, and an appropriate reagent is used for each of the operations.

SUMMARY

Provided are reagent supply devices and systems including same for analysis of a nucleic acid that may store a reagent for preparation of a nucleic acid sample and supply the reagent to a device for analysis of the nucleic acid. Additional aspects will be set forth in the description which follows and will be apparent from the description, or may be learned by practice of the presented embodiments.

According to an aspect of the present invention, a reagent supply device includes a plurality of chambers which are separated from each other such that different reagents may be injected, the plurality of chambers having bottom surfaces made of a membrane, wherein the membrane includes a destruction pattern which is formed at a position corresponding to each of the plurality of chambers, and the membrane is capable of being torn (breachable or rupturable) by an external impact to discharge the injected reagent from the chamber.

The reagent supply device may further include: a main body part having a membrane and a barrier rib structure forming spaces corresponding to the plurality of chambers; and a cover plate disposed on the main body part to cover the plurality of chambers, the cover plate having a plurality of openings forming respective inlets for the plurality of chambers. A reagent used for extracting a nucleic acid from a biological sample may be injected into the plurality of chambers.

The membrane and the main body part may be made of ductile polymer having a low reactivity with the reagent, for example, high density polyethylene ("HDPE"). The membrane has a thickness ranging from about 10 μm to about 1,000 μm. The destruction pattern may have an indented shape (e.g., embossed on the membrane) such that a thickness of the membrane within the destruction pattern is thin compared to regions of the membrane without the destruction pattern (i.e., the thickness of the membrane within the destruction pattern is less than the thickness of the membrane outside of the destruction pattern).

The plurality of chambers may include at least one of a sample chamber into which a biological sample is inserted; a washing buffer chamber into which a washing buffer for washing cells captured from the biological sample is injected; a lysis buffer chamber into which a lysis buffer for rupturing or crushing the captured cells to separate nucleic acids is injected; and a waste chamber for collecting discarded reagent. The sample chamber, the washing buffer chamber, and the lysis buffer chamber may have a bottom surface formed with a slope inclined toward the destruction pattern formed in each chamber.

The sample chamber may include a sample filter set for removing a foreign substance from the biological sample. The sample filter set may include a filter part and a top holder and a bottom holder fixing the filter part from top and bottom sides of the filter part. The top holder and the bottom holder may have cylindrical shapes, each having a surface with a lattice pattern, and the bottom holder and the top holder may have sizes and shapes such that the bottom holder may be inserted into the top holder. The filter part may be a film and the bottom holder may be inserted into the top holder in such a manner that the filter part is disposed on a lattice pattern surface of the bottom holder. The filter part may be a piece of foam and the bottom holder may be inserted into the top holder in such a manner that the filter part is disposed inside the bottom holder.

A plurality of cap sets for sealing the openings corresponding to the washing buffer chamber, the lysis buffer chamber, and the waste chamber may be provided. At least some of the plurality of cap sets may be made of an elastic material. Each of the plurality of cap sets may include: a cap member; an air permeable filter having a hydrophobic surface; and a filter holder fixing the filter to the cap member. The cap member may be formed with a hole for applying a pressure from outside. The hole may be sealed by tape and the tape may be removed when the reagent supply device is used.

A cover for the opening corresponding to the sample chamber among the plurality of openings of the cap plate may be provided. At least part of the cover may be made of an elastic material. An air permeable filter having a hydrophobic surface may be assembled with the cover. The cover may be formed with a hole for applying a pressure from outside. The hole may be sealed by tape and the tape may be removed when the reagent supply device is used.

A hook structure for facilitating coupling to inspection equipment in which the injected reagent is being used may be provided on an outer surface of the main body part.

BRIEF DESCRIPTION OF THE DRAWINGS

These and/or other aspects will become apparent and more readily appreciated from the following description of the embodiments, taken in conjunction with the accompanying drawings of which.

DETAILED DESCRIPTION

Reference will now be made in detail to embodiments, examples of which are illustrated in the accompanying drawings. In the drawings, like reference numerals refer to like elements throughout, and the dimensions of elements are exaggerated for clarity of illustration.

Figure 1:
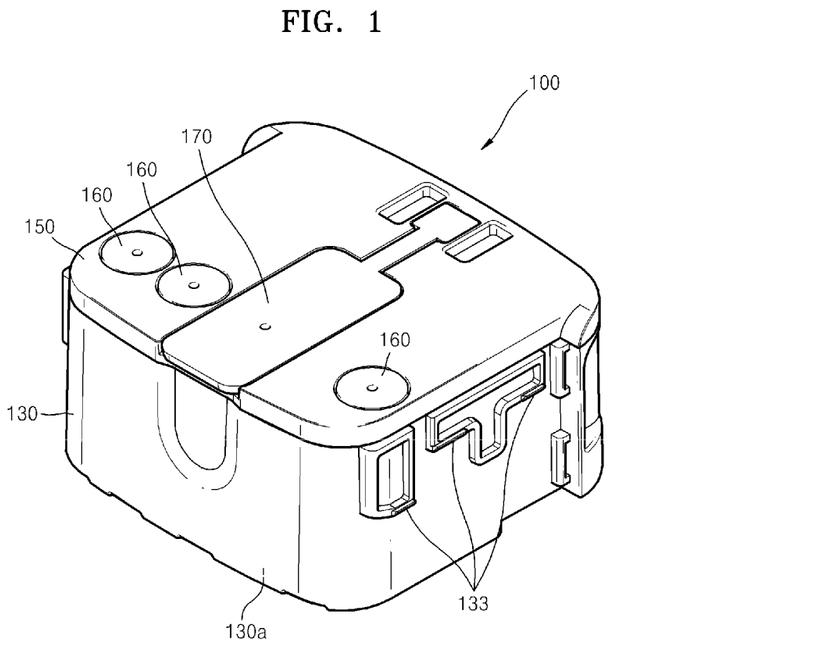
FIG. 1 is a perspective view illustrating a reagent supply device.
Figure 2:
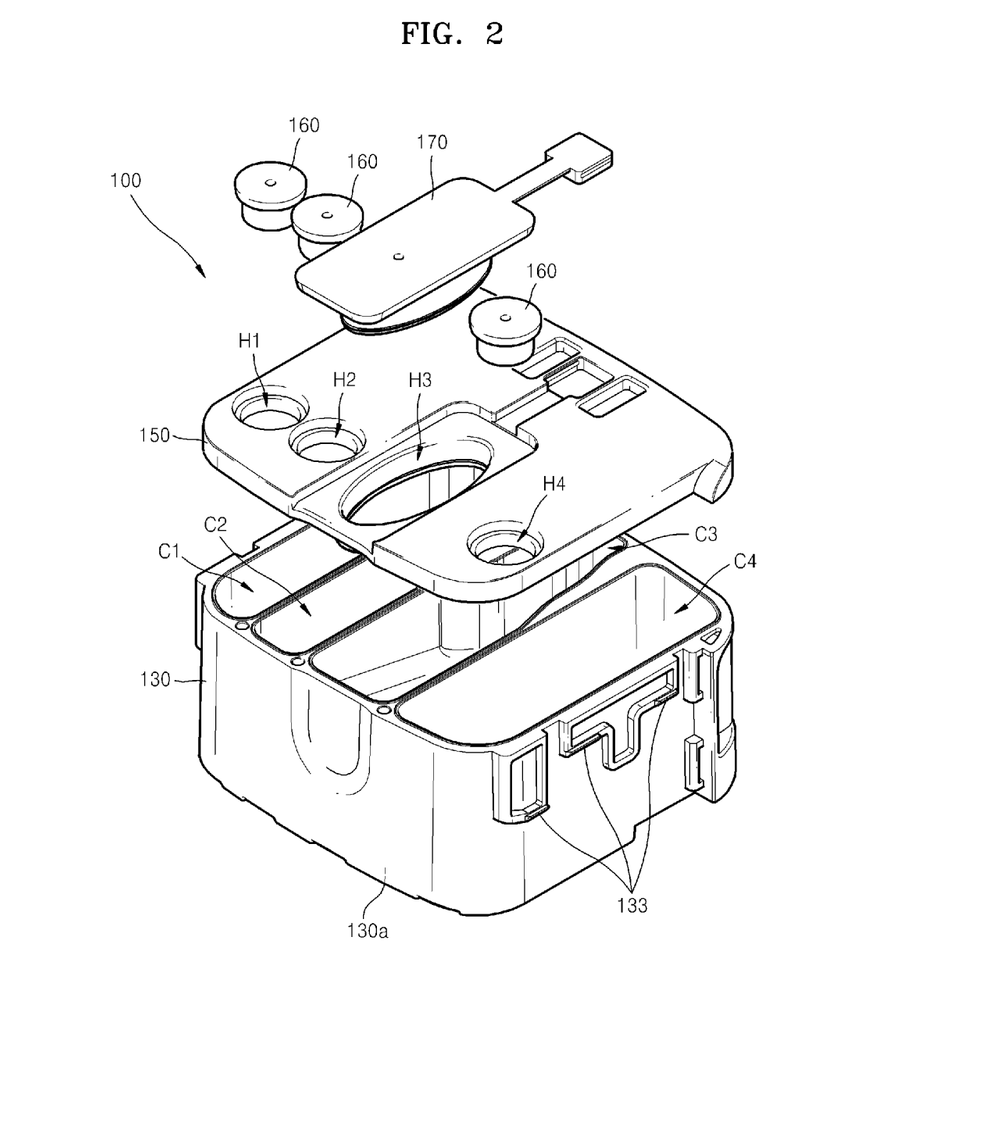
FIG. 2 is an exploded perspective view illustrating a detailed structure of the reagent supply device of FIG. 1.
Figure 3:
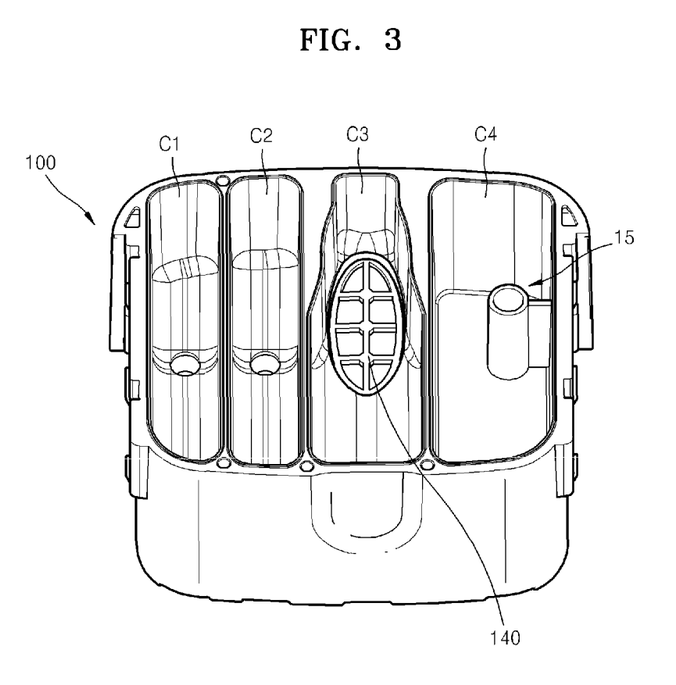
FIG. 3 is a perspective view illustrating a detailed internal structure of the chambers of the reagent supply device of FIG. 1.

FIG. 1 is a perspective view illustrating a reagent supply device 100. FIG. 2 is an exploded perspective view illustrating a detailed structure of the reagent supply device 100 of FIG. 1. FIG. 3 is a perspective view illustrating a detailed internal structure of the chambers of the reagent supply device 100 of FIG. 1.

According to an embodiment of the present invention, the reagent supply device 100 is a device which is able to store, transfer, and supply a reagent used in nucleic acid inspection equipment. Such inspection equipment may, for example, capture a specific cell from a sample using a microfluidic system, extract a nucleic acid, and determine whether a specific nucleic acid exists in the sample and, perhaps, the amount thereof using, for instance, an analytical or amplification technique such as polymerase chain reaction (PCR). For these operations, the reagent supply device 100 includes a plurality of chambers which are separated such that different reagents are able to be injected into and contained within the different chambers, the plurality of chambers having bottom surfaces made of a membrane, the membrane including a destruction pattern for destruction thereof, which is formed at a position corresponding to each of the plurality of chambers, and breachable or rupturable by an external impact to discharge the injected reagent from the chamber. In this respect, the bottom surface of each chamber may be formed of an individual membrane, or a single membrane can provide the bottom surfaces of several chambers by traversing the open area of several chambers.

Referring to FIGS. 1, 2, and 3, the reagent supply device 100 includes: a main body part 130 having a partition structure forming spaces corresponding to a plurality of chambers C1, C2, C3, and C4; a membrane forming a bottom surface 130a of the plurality of chambers C1, C2, C3, and C4; a cover plate 150 disposed on the main body part 130 to cover the plurality of chambers C1, C2, C3, and C4; and a plurality of openings H1, H2, H3, and H4 forming respective inlets for the plurality of chambers C1, C2, C3, and C4. Each of the chambers can have any size (volume) suitable for its intended use, such as for supplying reagents to a microfluidic device. Furthermore, the sizes of the chambers can be the same or different from one another. In some embodiments, each chamber will have a volume of less than about 2000 μl, such as about 1500 μl or less, or about 1000 μl or less.

Reagents used for extracting nucleic acids from a biological sample are injected into the plurality of chambers C1, C2, C3, and C4. Because the reagents are stored in the chambers C1, C2, C3, and C4 for a long time, the material for the main body part 150 is determined in consideration of hygroscopicity or reactivity with the reagents. The material for the main body part 150 may be a ductile polymer material having low reactivity with the reagent, for example, plastic. The polymer material may have hydrophobicity. The plastic may include polyethylene, polypropylene, polystyrene, polyacrylate, or combinations thereof. The polyethylene may be high density polyethylene having almost no reactivity with reagents used in the extracting of nucleic acids.

The plurality of chambers C1, C2, C3, and C4 may include a sample chamber C3 into which a biological sample becoming a clinical specimen is inserted; a washing buffer chamber C2 into which a washing buffer for washing cells captured from the biological sample is injected; a lysis buffer chamber C1 into which a lysis buffer for rupturing or crushing the captured cells to separate nucleic acids is injected; and a waste chamber C4 where the reagent remaining after being used for extraction of nucleic acids is discarded.

A sample filter set 140 for removing a foreign substance from the biological sample may be disposed in the sample chamber C3. The sample filter set 140 is disposed at an outlet of the sample chamber C3 and the destruction pattern is formed at a predetermined location of the bottom surface 130a corresponding to the outlet. When a clinical specimen, i.e., a sample, is inserted into the sample chamber C3, foreign substances may be inserted and mixed with the sample. In the case where these foreign substances are discharged from the reagent supply device 100 and then introduced into inspection equipment, the inspection equipment may become clogged or require a higher drive pressure to continue operating. Therefore, the sample filter set 140 may be employed so as to filter such foreign substances. The sample filter set 140 may be provided with a filter having pores that are a few microns (μm) in size, for example, in a range of about 0.1 μm to about 500 μm, and preferably about 1 μm to about 20 μm. Only the reagent which has passed through this filter to remove foreign substances may be discharged from the reagent supply device 100 and supplied to the inspection equipment.

The bottom surfaces of the sample chamber C3, the lysis buffer chamber C1, and the washing buffer chamber C2 are formed with slopes inclined toward their respective outlets. The destruction pattern is formed at a predetermined location of the bottom surface corresponding to the location of the outlet. Meanwhile, since in the case of the waste chamber C4, discarded reagent should not be again introduced into the inspection equipment, an introduction part 15 of the waste chamber C4 may be formed with a predetermined height and the bottom surface may be formed flat without a slope.

Hook structures 133 for facilitating the coupling of the reagent supply device 100 to the inspection equipment may be also formed at an outer surface of the main body part 130. The hook structures 133 may include a structure having a protruded pattern extending in a horizontal direction and a structure having a protruded pattern extending in a vertical direction. With these hook structures 133, the reagent supply device 100 may be inserted into the inspection equipment while staying level with the inspection equipment and may be coupled so as not to be released after being inserted.

Because the reagent supply device 100 functions to prevent foreign contamination substances from being introduced into the chambers C1, C2, C3, and C4 and to prevent an internal reagent from being unintentionally discharged from the chambers, the reagent supply device 100 is provided with a plurality of cap sets 160 and a cover 170 for sealing the openings H1, H2, H3, and H4 formed on the cover plate 150. The cap sets 160 seal the openings H1, H2, and H4, which correspond to the lysis buffer chamber C1, the washing buffer chamber C2, and the waste chamber C4. The cover 170 covers the opening H3 which corresponds to the sample chamber C3. At least some of the plurality of cap sets 160 and the cover 170 may be made of an elastic material. The plurality of cap sets 160 and the cover 170 may be formed with holes for applying a pressure (e.g., pneumatic or hydraulic pressure) to the chamber from outside when the cap is in place and an air permeable filter having a hydrophobic surface may be assembled with the cap set 160 and the cover 170. The holes formed in the plurality of cap sets 160 and the cover 170 may be sealed by using tape so that reagent does not evaporate. When the reagent supply device 100 is used, i.e., while the reagent supply device 100 is equipped in the inspection equipment to supply reagent, the tape may be removed so that a pressure may be applied to the chambers through these holes.

Figure 4A:
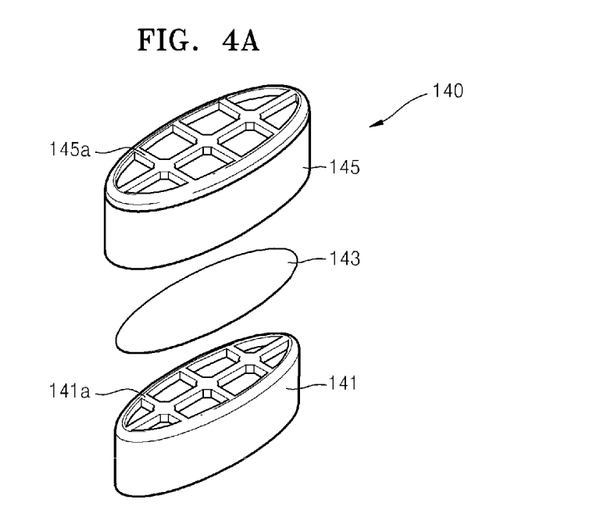
FIG. 4A is an exploded perspective view illustrating the detailed structure of a sample filter set employed in the reagent supply device of FIG. 1.

FIG. 4A is an exploded perspective view illustrating a detailed structure of a sample filter set 140 employed in the reagent supply device 100 of FIG. 1. The sample filter set 140 includes a filter part 143, and a top holder 145 and a bottom holder 141 fixing the filter part 143 between a top side and a bottom side thereof. The top holder 145 and the bottom holder 141 may have cylindrical shapes of which surfaces 145a and 141a have lattice patterns and may have sizes and shapes such that the bottom holder 141 may be inserted into the top holder 145. The filter part 143 may be a film as illustrated in FIG. 4A, and the bottom holder 141 may be inserted into the top holder 145 in such a manner that the filter part 143 is disposed on the lattice pattern surface 141a of the bottom holder 141.

Figure 4B:
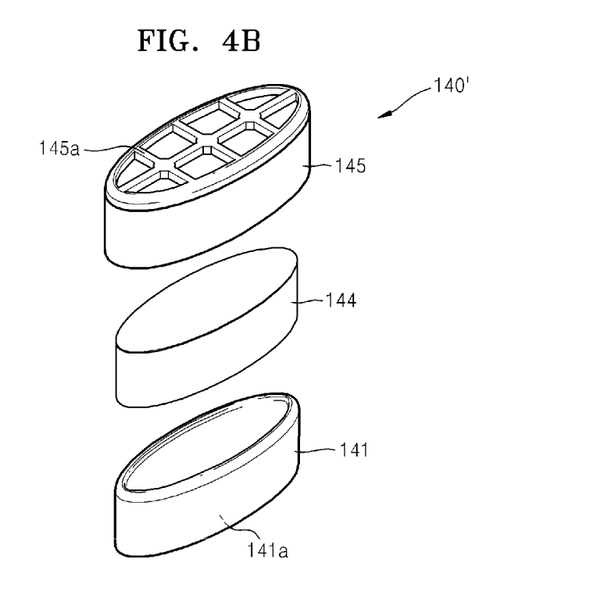
FIG. 4B is an exploded perspective view illustrating a modified example of the sample filter set of FIG. 4A.

FIG. 4B is an exploded perspective view illustrating a structure of a sample filter set 140' modified from the sample filter set of FIG. 4A. The filter part 144 may be a piece of foam as illustrated in FIG. 4B, and the bottom holder 141 may be inserted into the top holder 145 so that filter part 144 is disposed inside the bottom holder 141.

The sample filter set 140 of FIG. 4A or the sample filter set 140' of FIG. 4B may be selected in consideration of a filtration volume. To obtain a clinical specimen, a swab is typically used. For example, the filter part 143 with a thin film form as illustrated in FIG. 4A may be used in the case of a sample with fewer foreign substances, such as a nasal sample. The filter part 144 made of foam having a large filtration volume as illustrated in FIG. 4B may be used in the case of a sample containing many foreign substances other than cells, such as a stool sample. In each case, while the top holder 145 and the bottom holder 141 having the same structure may be used, the bottom holder 141 may be modified such that the bottom surface 141a is directed toward a top side or a bottom side of the filter part 143 or 144.

Figure 5:
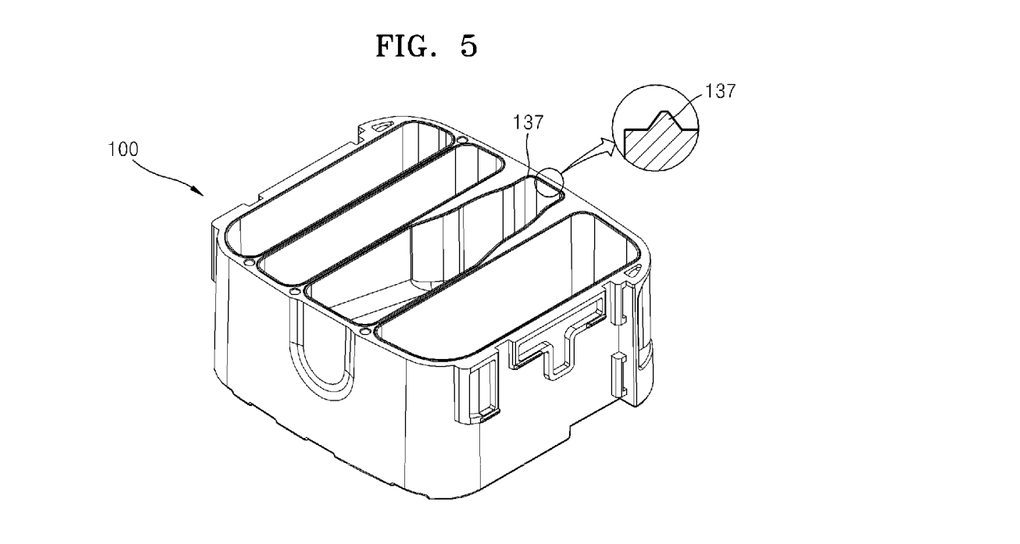
FIG. 5 is a perspective view illustrating a protrusion pattern for ultrasonic welding formed on an upper side of a main body part of the reagent supply device of FIG. 1.

FIG. 5 is a perspective view illustrating a protrusion pattern 137 for ultrasonic welding formed on an upper side of the main body part 130 in the reagent supply device 100 of FIG. 1. The protrusion pattern 137 is provided for ultrasonic welding between the main body part 130 and the cover plate 150 and the protrusion pattern 137 has a constant height formed along peripheries of the plurality of chambers C1, C2, C3, and C4. Using an adhesive to bond the main body part 130 to the cover plate 150 may cause problems, such as degeneration of bonding performance due to an injected reagent or contamination of the reagent due to fumes generated from the adhesive. However, a melting and bonding method using heat, such as ultrasonic welding, may prevent degeneration in bonding performance, contamination of the reagent, etc. The protrusion pattern 137 for ultrasonic welding may be formed on an upper surface of the main body part 130 or on a lower surface of the cover plate 150. The above-described configurations are only exemplary. Other arrangements of the protrusion pattern 137 sufficient for bonding the main body part 130 to the cover plate 150 may be contemplated by a person of ordinary skill in the art.

Figure 6:
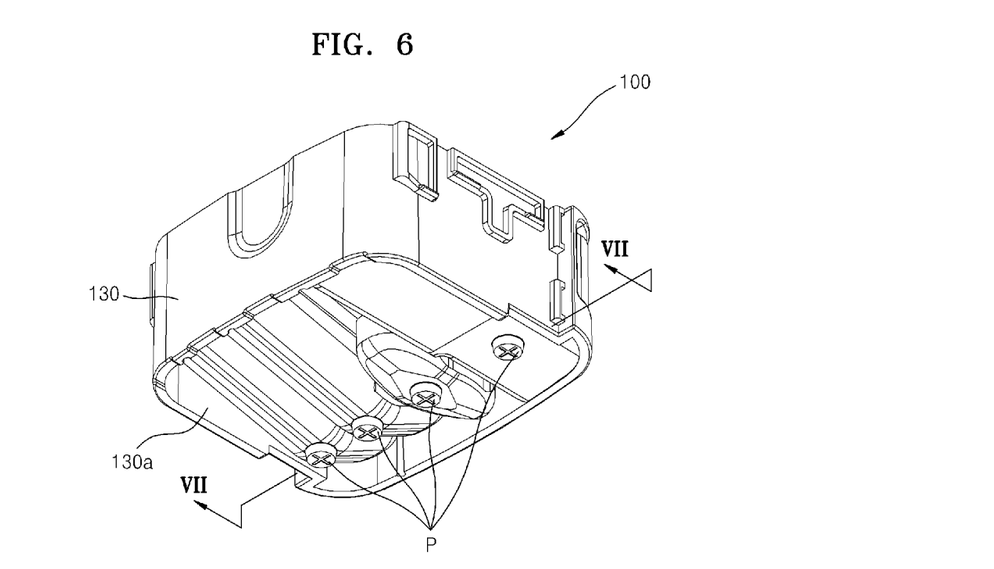
FIG. 6 is a perspective view illustrating the bottom surface of the reagent supply device of FIG. 1.
Figure 7A:
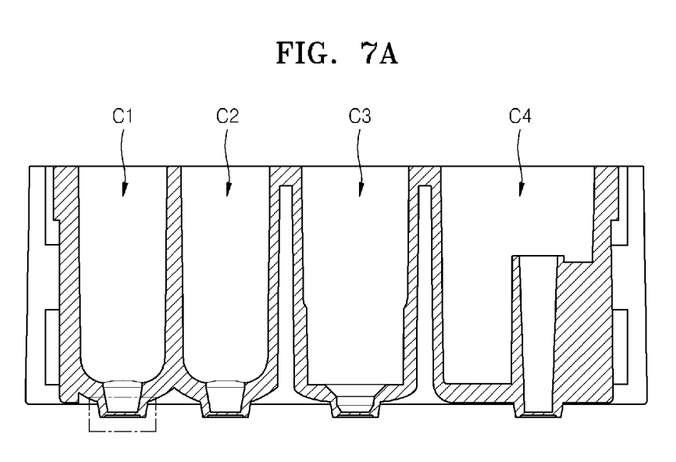
FIG. 7A is a cross-sectional view taken along a line VII-VII of FIG. 6.
Figure 7B:
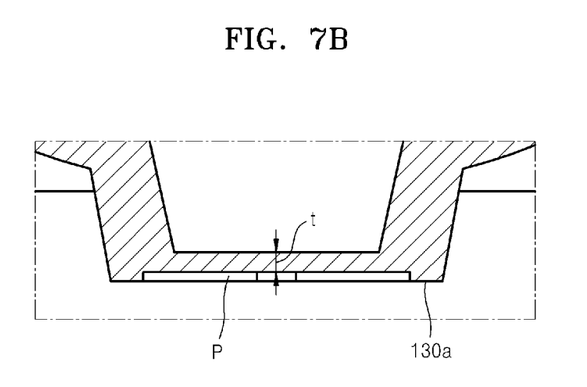
FIG. 7B is a partial detailed view of FIG. 7A.

FIG. 6 is a perspective view illustrating the bottom surface 130a of the reagent supply device 100 of FIG. 1, FIG. 7A is a cross-sectional view taken along a line VII-VII of FIG. 6, and FIG. 7B is a partial detailed view of FIG. 7A.

Referring to FIGS. 6, 7A, and 7B, the bottom surface 130a of the reagent supply device 100 is made of a membrane, the membrane being formed with a destruction pattern P at a location corresponding to each of the plurality of chambers C1, C2, C3, and C4. The thickness of the membrane is determined such that the chambers C1, C2, C3, and C4 may be stably formed and the membrane is breachable or rupturable by a proper force so as to discharge the reagent from the chamber. The destruction pattern P may be destroyed by an external impact, for example, by a structure such as a needle that is part of the inspection equipment. The thinner the membrane the easier the membrane is torn although a force contacting the needle of the inspection equipment is small and thus the possibility that the reagent flows out increases. On the contrary, when the membrane is too thick, the membrane is not easily torn even by great force. Considering this, the membrane may be formed in a thickness range of about 10 to about 1,000 µm, and preferably about 100 to about 300 µm. The membrane may be formed of the same material as the material for the main body part 130, for example, a polymer having a high ductility, such as HDPE.

The destruction pattern P may have an indented shape such that the thickness of the membrane within the destruction pattern is thin compared to regions of the membrane without the destruction pattern. That is, the thickness t of the membrane where the destruction pattern P is formed may be formed thinner than other regions. The shape of the destruction pattern P may be designed so as to increase rigidity and tearing characteristics of the membrane, for example, by having a cross-shaped (†) pattern as illustrated in FIG. 6.

Figure 8:
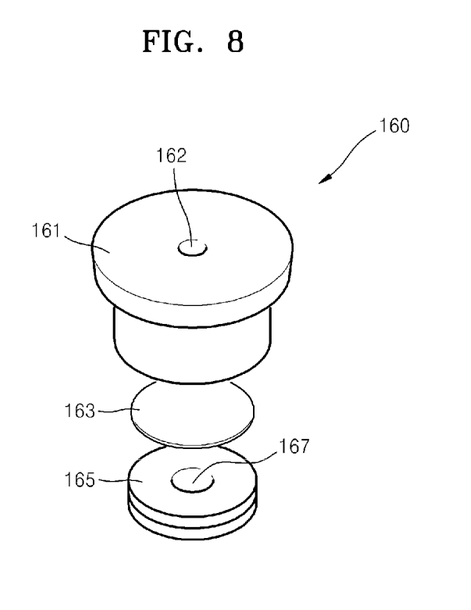
FIG. 8 is an exploded perspective view illustrating a structure of a cap set employed in the reagent supply device of FIG. 1.

FIG. 8 is an exploded perspective view illustrating the structure of a cap set 160 employed in the reagent supply device 100 of FIG. 1. The cap set 160 includes a cap member 161, an air permeable filter 163 having a hydrophobic surface, and a filter holder 165 fixing the filter 163 to the cap member 161. At least part of the cap set 160, for example, the cap member 161, may be made of an elastic material.

The cap member 161 has a shape which is inserted into the holes H1, H2, and H4 of the cover plate 150 and fixed to the cover plate 150 to form a seal, thus protecting the reagent injected into the chambers. The air permeable filter 163 with a hydrophobic surface is provided such that the injected reagent does not leak from the chamber. The filter holder 165 is provided to fix the filter 163 to the cap member 161. When the reagent supply device 100 operates, a pressure may be applied to the chambers through a hole 162 formed on the cap member 161 and a hole 167 formed on the filter holder 165. Because the filter 163 is air-permeable but prevents liquid reagent from flowing out of the chambers, the filter 163 may not prevent evaporation of the reagent. Therefore, the hole 162 formed on the cap member 161 may be sealed with tape, and when the reagent supply device 100 is used, the tape may be removed.

Figure 9:
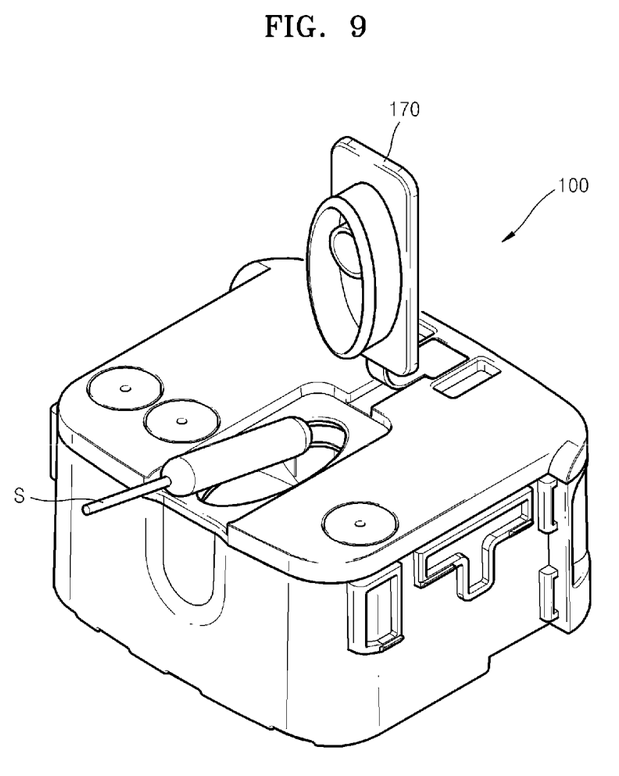
FIG. 9 is a perspective view illustrating a sample swab being inserted into an opening in the cap plate of the reagent supply device of FIG. 1.

FIG. 9 is a perspective view illustrating the reagent supply device 100 of FIG. 1 with cover 170 opened and a sample on swab S inserted into sample chamber C3 through opening H3. If swab S is too long, it may be cut to an appropriate length so as to permit closure of cover 170.

An assembling process of the reagent supply device 100 with the above-described elements will now be described. The assembling process of the reagent supply device 100 may be, for example, an operation of preparing a sample which is being used in a PCR. First, the main body part 130 and the cover plate 150 are bonded by ultrasonic welding. The bonding is not limited to ultrasonic welding and may also be performed by using an adhesive or an adhesive tape, among other bonding methods. Next, the sample filter set 140 is inserted into the sample chamber C3 through the opening H3 of the cover plate 150. A suitable amount (e.g., about 300 μl) of a lysis buffer is injected into the lysis buffer chamber C1 and then the lysis buffer chamber C1 is sealed by the cap set 160. A suitable amount (e.g., about 500 μl) of a washing buffer is injected into the washing buffer chamber C2 and then the washing buffer chamber C2 is sealed by the cap set 160. A suitable amount (e.g., about 1,000 μl) of a washing buffer is injected into the sample chamber C3 and then the sample chamber C3 is sealed by the cover 170. The waste chamber C4 is sealed by the cap set 160. The holes formed on the cap set 160 and the cover 170 are sealed with tape or the like. The cover 170 is opened, a harvested sample in the form of a swab is placed in the sample chamber C3, cover 170 is closed, and the sample chamber C3 is vortexed or otherwise agitated. The reagent supply device 100 prepared as above is then coupled to the inspection equipment.

The reagent supply device 100 may store and transfer a variety of reagents for sample inspection and may supply the reagents to the inspection equipment. As described above, according to one or more of the above embodiments of the present invention, a reagent supply device has a structure that is able to store a variety of reagents and a sample in the form of a swab harvested from a clinical specimen in separate chambers. After the reagent supply device is coupled to an inspection device, the reagent supply device is able to supply the reagent to inspection equipment when a membrane of a bottom surface of the reagent supply device is torn at a predetermined location. Accordingly, the process of preparing reagents and samples for analysis of nucleic acids may be very conveniently completed. In this respect, the invention also provides a reagent supply system comprising the reagent supply device as described herein and reagents contained within one or more chambers of the device. The reagent supply device and reagents contained in the chambers thereof are as previously described. The reagent supply system may further include an inspection device that detects, amplifies, or otherwise analyzes a nucleic acid, such as a PCR device.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A reagent supply device comprising:
   a plurality of chambers which are separated from each other such that different reagents may be contained therein, the plurality of chambers each having a bottom surface made of a membrane, the membrane comprising a destruction pattern which is formed at a position corresponding to each of the plurality of chambers and breachable by an external impact to discharge a reagent from the chamber;
   wherein a thickness of the membrane within the destruction pattern is less than a thickness of the membrane outside of the destruction pattern;
   a main body part comprising the membrane and a partition structure forming spaces corresponding to the plurality of chambers;

a cover plate disposed on the main body part opposite the membrane and comprising a plurality of openings forming inlets for each of the plurality of chambers, respectively;

a plurality of cap sets for sealing the openings of the cover plate, wherein each of the plurality of cap sets comprises: a cap member;

an air permeable filter having a hydrophobic surface; and a filter holder fixing the air permeable filter to the cap member, wherein the cap member is formed with a hole for applying pressure to the chamber, wherein at least one of the plurality of chambers has a bottom surface within the chamber formed with a slope inclined toward the destruction pattern, Wherein the plurality of chambers comprise a chamber having a sample filter set disposed at an outlet thereof.

2. The reagent supply device of claim 1, wherein the main body part is made of a ductile polymer having a low reactivity with the reagent.

3. The reagent supply device of claim 2, wherein the ductile polymer is high density polyethylene (HDPE).

4. The reagent supply device of claim 1, wherein the membrane has a thickness of about 10 μm to about 1,000 μm.

5. The reagent supply device of claim 1, wherein the destruction pattern has an indented shape formed on the membrane such that the thickness of the membrane within the destruction pattern is thin compared to regions of the membrane without the destruction pattern.

6. The reagent supply device of claim 1, wherein the sample filter set comprises:

a filter part with top and bottom sides; and a top holder and a bottom holder for fixing a location of the filter part with respect to the sample chamber.

7. The reagent supply device of claim 6, wherein the top holder and the bottom holder have cylindrical shapes, each holder having a surface with a lattice pattern, and the bottom holder is configured to be inserted into the top holder.

8. The reagent supply device of claim 7, wherein the filter part is a film and the bottom holder is inserted into the top holder in such a manner that the filter is disposed on the lattice pattern surface of the bottom holder.

9. The reagent supply device of claim 6, wherein the filter part is a piece of foam and the bottom holder is inserted into the top holder in such a manner that the filter part is disposed inside the bottom holder.

10. The reagent supply device of claim 1, wherein at least two of the plurality of cap sets are made of an elastic material.

11. The reagent supply device of claim 1, wherein the hole is sealed by a tape and the tape is removed when the reagent supply device is used.

12. The reagent supply device of claim 1, wherein the main body part includes a hook structure for facilitating coupling to inspection equipment in which the injected reagent is being used.

* * * * *